United States Patent [19]

Shaw

[11] Patent Number: 4,560,673

[45] Date of Patent: Dec. 24, 1985

[54] CATALYST FOR THE OXIDATION OF UNSATURATED ALDEHYDES

[75] Inventor: Wilfrid G. Shaw, Lyndhurst, Ohio

[73] Assignee: The Standard Oil Company, Cleveland, Ohio

[21] Appl. No.: 713,953

[22] Filed: Mar. 20, 1985

Related U.S. Application Data

[62] Division of Ser. No. 560,289, Dec. 12, 1983.

[51] Int. Cl.$^4$ .................. B01J 21/06; B01J 23/22; B01J 23/28; B01J 23/72
[52] U.S. Cl. .................. 502/206; 502/303; 502/306; 502/307; 502/308; 502/309; 502/310
[58] Field of Search .............. 502/206, 303, 306, 307, 502/308, 309, 310; 562/535

[56] References Cited

U.S. PATENT DOCUMENTS

| | | | |
|---|---|---|---|
| 4,051,180 | 9/1977 | Shaw et al. | 502/308 X |
| 4,289,654 | 9/1981 | Bertolini et al. | 502/306 X |
| 4,359,407 | 11/1982 | Dolhyj et al. | 502/308 X |

FOREIGN PATENT DOCUMENTS 5195014  8/1976  Japan ................................ 562/535

Primary Examiner—W. J. Shine
Attorney, Agent, or Firm—Charles S. Lynch; John E. Miller, Jr.; Larry W. Evans

[57] ABSTRACT

A vapor phase catalytic process for making acrylic acid from acrolein by oxidation thereof with molecular oxygen, optionally in the presence of steam. A new catalyst comprising a complex oxide catalyst of Mo, V and Zr.

4 Claims, No Drawings

CATALYST FOR THE OXIDATION OF UNSATURATED ALDEHYDES

This is a division of application Ser. No. 560,289 filed 12/12/83.

This invention relates to oxidation of olefinically unsaturated aldehydes using novel MoVZr oxide catalysts. In a more specific aspect there is provided a process for the oxidation of acrolein to acrylic acid.

It is an object of the present invention to provide a process for the oxidation of an olefinically unsaturated aldehyde, particularly acrolein, to the corresponding unsaturated carboxylic acid, acrylic acid, by the use of a novel catalyst.

It is another object of the present invention to provide a novel catalyst effective for such reaction comprising a catalyst containing Mo, V and Zr in oxide form.

Other objects, as well as aspects, features and advantages, of the present invention will become apparent from a study of the specification, including the specific examples and the claims.

These objects are realized according to the present invention in which there is provided a vapor phase process for producing acrylic acid from acrolein by oxidation of the unsaturated aldehyde with molecular oxygen, optionally in the presence of steam, and in the presence of a complex oxide catalyst having the elements and the ratios thereof represented by the empirical formula $$Mo_aV_bZr_cX_dY_eO_f$$

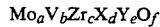

wherein X is one or more of Cu and Mg. In the above formula Y can be one or more of K, Rb, Cs, Sn, Ti, Cr, Re, Sb, Mn, Ge, Ca, Ba, Zn, Ag, Cd, La, As, Bi and B. Y can also be or include tungsten, although usually my catalysts are substantially free of tungsten. Good MoVW catalysts for acrolein oxidation are known; therefore, the addition of some W to the present MoVZr catalysts can be practiced but is usually not.

In the above catalyst formula
a is 6-18, usually 9-15
b is 0.1-10, usually 0.5-5
c is 0.05-5, usually 0.1-3
d is 0-3, usually 0.1-3
e is 0-2, usually 0.01-2
f is a number sufficient to satisfy the valence requirements of the other elements present, and
the active catalyst is essentially free of P, Ce, Fe, Al and Ni.

In the above catalysts the subscripts can be
a=9-15
b=0.5-5
c=0.1-3
d=0.01-2
e=0-1
f is a number sufficient to satisfy the valence requirements of the other elements present.

In addition to the active catalytic ingredients, the catalysts of the invention or used in the process of the invention, can contain a support material. Suitable support materials include silica, zirconia, silicon carbide, boron phosphate and the like. When alumina is used as a support it is used in the form of preformed, fused essentially non-porous alumina support particles on which the catalyst is coated. An especially useful non-porous fused alumina support material is Alundum.

The catalysts of the present invention are capable of very selectively oxidizing acrolein to acrylic acid at low temperatures, as illustrated by the examples in Table 1.

The oxidation of unsaturated aldehydes to obtain the corresponding acid is well known in the art. Basically, the invention, with respect to the process, is the use of the new catalyst within the general parameters of the known art process.

Ratios of feeds can vary considerably with molecular oxygen to aldehyde molar ratios varying from about 0.5 to about 5, steam from a small amount generated in the reaction to 20 or more moles of steam per mole of aldehyde. Effluent gas can also be recycled in lieu of or as a supplement to steam. This gas contains significant amounts of nitrogen plug some oxides of carbon, and steam as the major components. In the usual practice, about 1 to 10 moles of steam or recycled gas are added to the reactant feed. Usual reaction temperatures are in the range from 250° to 400° C., more often from 275°-350° C.

The reaction can be effected in any suitable reactor, such as a fixed catalyst bed, a fluidized bed or a gravity flowing bed of catalyst.

The apparent contact time can be on the order of about 0.1 to 20 seconds but contact times of 0.5 to 5 seconds are more usual.

The catalysts are prepared by methods generally known in the art for making oxide catalysts.

Normally, the catalysts of the invention are prepared by mixing the catalyst ingredients in the proper proportions in an aqueous mixture, drying the resulting aqueous slurry and calcining the product. The ingredients going into the preparation of the catalysts can be the oxides, halides, nitrates, acetates, or other salts of the particular compound added. If a support is used, the material comprising the support can be incorporated into the catalyst along with the other ingredients, or the active component can be coated onto the moistened support in the manner shown for somewhat similar catalyst in U.S. Pat. No. 3,956,377, incorporated herein for its method teachings; and in the manner illustrated in specific examples herein.

In any event, after the precursor compounds for the active catalyst, with or without the support material, if any, have been combined to form an aqueous slurry, the slurry is evaporated to dryness, and the dried solid obtained is heated in the presence of air at temperatures between about 200° and 600° C., usually about 250°-500° C. This calcination can take place outside of the catalytic reactor or an in situ activation can be utilized.

The following illustrative examples of the invention illustrate the efficacy of the catalysts of the invention, but should not in any way be considered as limiting.

EXAMPLE 1 (Comparative)

Preparation of $Mo_{12}V_3O_x$ was made by the following procedure:

To 200 ml of hot distilled water was added 31.78 grams of ammonium heptamolybdate. After dissolution with heating and stirring, 5.26 grams of ammonium metavanadate were added and readily dissolved, then one gram of 85 percent hydrazine hydrate was added. The solution was evaporated to near dryness with continual heating and stirring, and then the contents were placed in a dryingg oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 2

Preparation of $Mo_{12}V_3Zr_{0.3}O_x$ was made by the following procedure:

To 200 ml of hot distilled water was added 31.20 grams of ammonium heptamolybdate. After dissolution with heating and stirring, 5.18 grams of ammonium metavanadate and 1.31 grams of zirconyl diacetate tetrahydrate were added and readily dissolved, then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 3

Preparation of $Mo_{12}V_3Zr_{0.7}O_x$ was made by the following procedure:

To 200 ml of hot distilled water was added 30.47 grams of ammonium heptamolybdate. After dissolution with heating and stirring, 5.10 grams of ammonium metavanadate and 2.99 grams of zirconyl diacetate tetrahydrate were added and readily dissolved, then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 4

Preparation of $Mo_{12}V_{1.8}Zr_{0.3}O_x$ was made by the following procedure:

To 200 ml of hot distilled water was added 32.97 grams of ammonium heptamolybdate. After dissolution with heating and stirring, 3.31 grams of ammonium metavanadate and 1.39 grams of zirconyl acetate were added and readily dissolved, then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 5 (Comparative)

Preparation of $Mo_{12}V_3Cu_{0.2}O_x$ was made by the following procedure:

To 200 ml of hot distilled water was added 31.53 grams of ammonium heptamolybdate. After dissolution with heating and stirring, 5.28 grams of ammonium metavanadate and 0.60 grams of copper diacetate were added and readily dissolved, then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 6

Preparation of $Mo_{12}V_3Zr_{0.3}Cu_{0.2}O_x$ was made by the following procedure:

To 200 ml of hot distilled water was added 30.96 grams of ammonium heptamolybdate. After dissolution with heating and stirring, 5.18 grams of ammonium metavanadate and 0.59 grams of copper diacetate and 1.30 grams of zirconyl acetate were added and readily dissolved, then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 7

Preparation of $Mo_{12}V_3Zr_{0.3}CuO_x$ was made by the following procedure:

To 200 ml of hot distilled water was added 30.03 grams of ammonium heptamolybdate. After dissolution with heating and stirring, 4.97 grams of ammonium metavanadate, and 2.83 grams of copper diacetate and 1.26 grams of zirconyl acetate were added and readily dissolved, then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 8

Preparation of $Mo_{12}V_3Zr_{0.3}Cu_{0.5}O_x$ was made by the following procedure:

To 200 ml of hot distilled water was added 30.6 grams of ammonium heptamolybdate. After dissolution with heating and stirring, 5.06 grams of ammonium metavanadate, and 1.44 grams of copper diacetate and 0.90 grams of zirconyl acetate were added and readily dissolved, then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 9

Preparation of $Mo_{12}V_3Zr_{0.3}Cu_{0.5}Rb_{0.1}O_x$ was made by the following procedure:

To 200 ml of hot distilled water was added 31.62 grams of ammonium heptamolybdate. After dissolution with heating and stirring, 4.98 of ammonium metavanadate, and 1.42 grams of copper diacetate, 1.26 grams of zirconyl acetate and 0.17 grams of rubidium hydroxide were added and readily dissolved. then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 10

Preparation of $Mo_{12}V_4Zr_{0.3}Cu_{0.5}O_x$ was made by the following procedure:

To 200 ml of hot distilled water was added 29.32 grams of ammonium heptamolybdate. After dissolution with heating and stirring, 6.54 grams of ammonium metavanadate, 1.39 grams of copper diacetate and 1.23 grams of zirconyl acetate were added and readily dissolved, then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

EXAMPLE 11

Preparation of $Mo_{12}V_3Zr_{0.1}Mg_{0.5}O_x$ was made by the following procedure:

To 200 ml of hot distilled water was added 32.85 grams of ammonium heptamolybdate. After dissolution with heating and stirring, 5.18 grams of ammonium metavanadate, 1.58 grams of magnesium acetate and 0.44 grams of zirconyl acetate were added and readily dissolved, then one gram of 85 percent hydrazine hydrate was added. The solution was evaporated to near dryness with continual heating and stirring, and then the contents were placed in a drying oven at approximately 110° C. for 16 hours. The dried material was crushed and ground to pass through a 50 mesh screen. A sufficient amount of powder was employed to coat ⅛" Alundum spheres, which had been premoistened, to achieve a twenty weight percent coating on the spheres. The coated spheres were then dried at 110° C. in the drying oven and then activated by heat treating at 370° C. for two hours.

The catalysts prepared above were placed in a fixed-bed downflow reactor constructed of 1.0 cm. inside diameter stainless steel tubing having a reaction zone of 20 cc. The reactor was heated in a split block furnace. the reactor was fed with a mixture of acrolein/air/nitrogen/steam in the molar ratio of 1/8.5/2.4/6.2. The reaction was conducted at atmospheric pressure, and the apparent contact time was as shown in Table 1. The temperatures of the surrounding block employed in the reactions are given in Table 1, and the results given in the Table are in terms of the following definitions:

$$\text{Percent Conversion} = \frac{\text{Moles of acrolein reacted} \times 100}{\text{Moles of acrolein fed}}$$

$$\text{Percent Yield} = \frac{\text{Moles of product recovered} \times 100}{\text{Moles of acrolein fed}}$$

$$\text{Percent Selectivity} = \frac{\text{Moles of acrylic acid recovered} \times 100}{\text{Moles of acrolein reacted}}$$

TABLE 1

| Catalyst Example No. | Reaction Temp., C.° | Contact Time Seconds | % Conv. of Acrolein | Corrected* % Yield of Acrylic Acid | Acetic Acid | Percent Selectivity to Acrylic Acid |
|---|---|---|---|---|---|---|
| 1 | 356(a) | 1.7 | 47.6 | 34.2 | 0.9 | 71.8 |
| 2 | 308 | 1.8 | 96.0 | 90.9 | 1.2 | 94.6 |
| 3 | 329(a) | 1.7 | 96.7 | 90.2 | 1.2 | 93.2 |
| 4 | 341(a) | 1.7 | 95.4 | 87.4 | 1.4 | 91.6 |
| 5 | 310(a) | 1.8 | 55.4 | 50.7 | 0.3 | 91.6 |
| 6 | 304(a) | 1.8 | 94.2 | 87.5 | 1.8 | 92.9 |
| 7 | 287(b) | 1.9 | 99.2 | 96.4 | 0.8 | 97.1 |
| 8 | 276(a) | 1.9 | 99.0 | 95.4 | 0.8 | 96.4 |
| 9 | 298 | 1.9 | 99.8 | 95.6 | 1.1 | 95.8 |
| 10 | 293(a) | 1.8 | 95.6 | 91.2 | 0.7 | 95.4 |
| 11 | 298(b) | 1.9 | 99.5 | 95.2 | 0.9 | 95.7 |

*Corrected to 100% carbon balance. All carbon balances were 95–105% of theory.
(a)Catalyst given 30 minutes at 400° C. at feed conditions prior to test data at indicated temperature.
(b)Catalyst given 30 minutes at 360° C. at feed conditions prior to test data at indicated temperature.

The foregoing examples of Table 1 illustrate the excellent conversions, yields and selectivities possible with the present catalysts, as compared to Examples 1 and 5 which did not contain the zirconium component of the catalysts of the present invention.

As will be evident to those skilled in the art various modifications of this invention can be made or followed in the light of the foregoing disclosure and discussion without departing from the spirit and scope of the disclosure or from the scope of the claims.

I claim:

1. A complex oxide catalyst consisting essentially of the elements and the ratios thereof represented by the empirical formula:

$$Mo_a V_b Zr_c X_d Y_e O_f$$

wherein
X is one or more of Cu and Mg;
Y is one or more of K, Rb, Cs, Sn, Ti, Cr, Re, Sb, Mn, Ge, Ca, Ba, Zn, Ag, Cd, La, As, Bi, B and W, and
a is 9–15;
b is 0.5–5;
c is 0.1–3;
d is 0.01–2;
e is 0–1;
f is a number sufficient to satisfy the valency requirements of the other elements present, and
wherein the catalyst is essentially free of P, Ce, Al, Fe and Ni.

2. A complex oxide catalyst consisting essentially of the elements and the ratios thereof represented by the empirical formula:

$$Mo_a V_b Zr_c X_d Y_e O_f$$

wherein
X is one or more of Cu and Mg;
Y is one or more of K, Rb, Cs, Sn, Ti, Cr, Re, Sb, Mn, Ge, Ca, Ba, Zn, Ag, Cd, La, As, Bi, and B, and
a is 9–15;
b is 0.5–5;
c is 0.1–3;
d is 0.01–2;
e is 0–1;
f is a number sufficient to satisfy the valency requirements of the other elements present, and
wherein the catalyst is essentially free of P, Ce, Al, Fe, W and Ni.

3. A catalyst of claim 2 which contains Cu.

4. A catalyst of claim 2, which contains Mg.